(12) United States Patent
Lee et al.

(10) Patent No.: US 11,712,512 B2
(45) Date of Patent: Aug. 1, 2023

(54) AMBULATORY MEDICAL PUMP CARTRIDGE LOCKING SYSTEM

(71) Applicant: Zyno Medical, LLC, Natick, MA (US)

(72) Inventors: Chaoyoung Lee, Weston, MA (US); Zhenhua Mao, Andover, MA (US); Frederick Lee, Boston, MA (US); Mei Zhang, Sharon, MA (US)

(73) Assignee: Zyno Medical, LLC, Natick, MA (US)

( * ) Notice: Subject to any disclaimer, the term of this patent is extended or adjusted under 35 U.S.C. 154(b) by 503 days.

(21) Appl. No.: 16/879,485

(22) Filed: May 20, 2020

(65) Prior Publication Data
US 2021/0361855 A1 Nov. 25, 2021

(51) Int. Cl.
*A61M 5/142* (2006.01)
*A61M 5/14* (2006.01)

(52) U.S. Cl.
CPC .......... *A61M 5/142* (2013.01); *A61M 5/1418* (2013.01); *A61M 2005/14208* (2013.01); *A61M 2205/121* (2013.01)

(58) Field of Classification Search
CPC .............. A61M 5/142; A61M 2205/12; A61M 2205/121; A61M 5/1413; H02B 1/052; H02B 1/0523; H02B 1/0526; H01R 13/00; H01R 13/62; H01R 13/627; H01R 13/6271; H01R 13/6272; H01R 13/6273; H01R 13/6275; H01R 13/62933; H01R 24/00; Y10T 292/432; Y10T 403/7015; Y10T 403/7045; F16B 5/07; F16B 5/0657; F16B 5/0621; F16P 3/08; B65D 55/02
See application file for complete search history.

(56) References Cited

U.S. PATENT DOCUMENTS

| 4,565,542 A * | 1/1986 | Berg ..................... A61M 5/142 604/153 |
| 5,993,420 A | 11/1999 | Hyman et al. |
| 2016/0058940 A1 * | 3/2016 | Zhang ............... A61M 5/14244 604/67 |
| 2017/0028126 A1 | 2/2017 | Moosai |
| 2019/0099552 A1 | 4/2019 | Zhang et al. |

FOREIGN PATENT DOCUMENTS

| EP | 0182502 | 5/1986 |
| WO | 2017106108 | 6/2017 |

OTHER PUBLICATIONS

Smiths Medical, CADD-Solis 2110 Ambulatory Infusion Pump Operator's Manual, Software version 4.2, 2019 (Year: 2019).*

* cited by examiner

*Primary Examiner* — Nathan R Price
*Assistant Examiner* — Anna E Goldberg-Richmeier
(74) *Attorney, Agent, or Firm* — Boyle Fredrickson S.C.

(57) ABSTRACT

A low-cost medical pump for ambulatory use provides an improved IV line cartridge attachment allowing for single handed, low force release while preventing inadvertent IV line cartridge release. A rotatable side lever minimizes the force required to move the locking elements against a spring biased force urging the locking elements to a locking position.

17 Claims, 2 Drawing Sheets

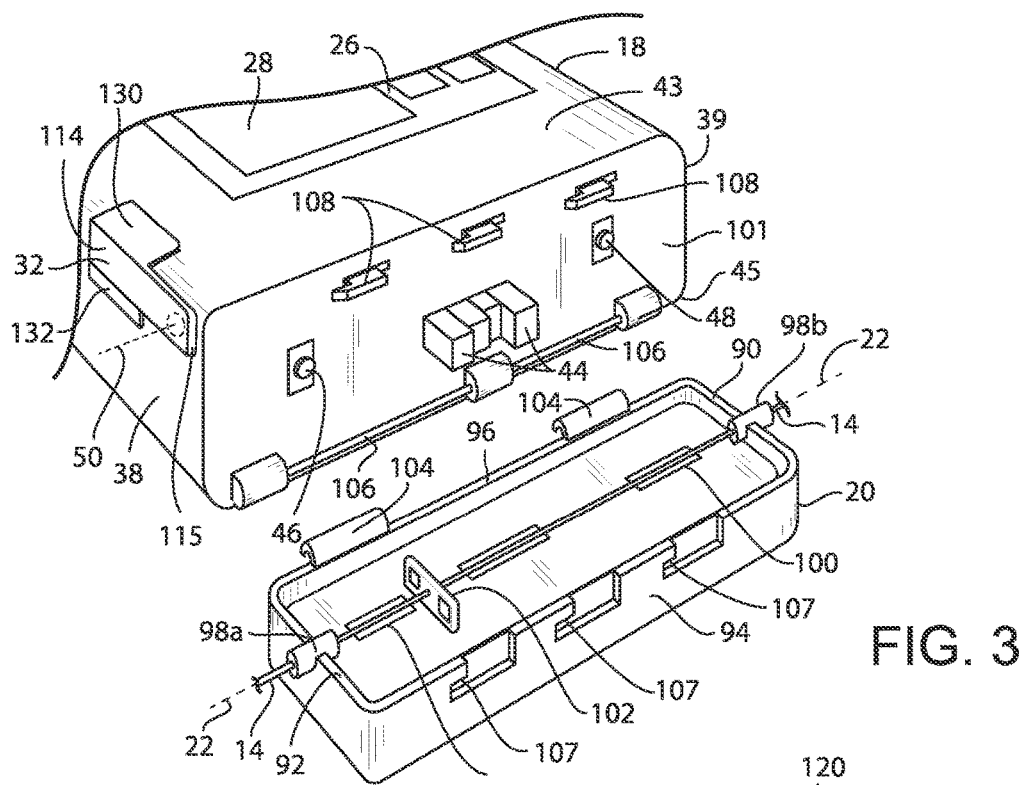
FIG. 3
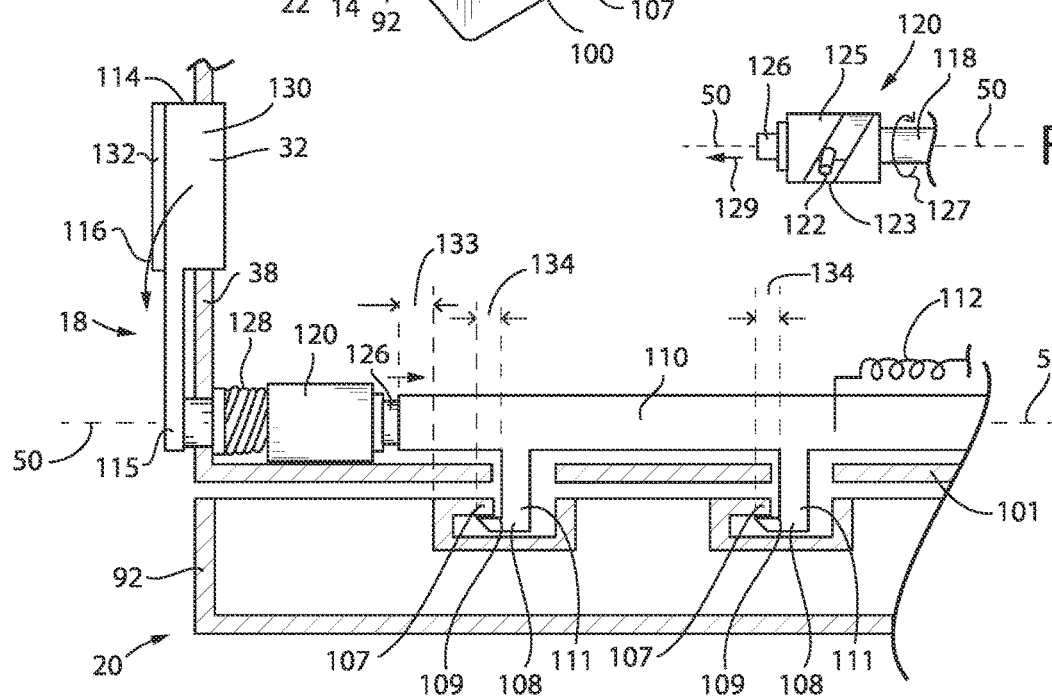
FIG. 5
FIG. 4

AMBULATORY MEDICAL PUMP CARTRIDGE LOCKING SYSTEM

CROSS-REFERENCE TO RELATED APPLICATION

N/A

BACKGROUND OF THE INVENTION

The present invention relates to compact infusion pumps for ambulatory use and in particular to an infusion pump design to reduce the costs of medical care delivery.

Medical pumps, such as infusion pumps, are known for computer-controlled delivery of medication (henceforth medicaments) to patients over a period of time. Recently, battery-powered compact infusion pumps have become available that permit the patient to remain active (ambulatory), for example, in a home environment away from a clinic or hospital during the treatment.

Typically, the medicament is provided in a flexible bag that may be connected to an IV line which in turn attaches to a needle or port communicating with the patient. A nurse or other health care professional ministering to the patient receives the medicament, reviews the medicament description for correctness, and enters the desired dose and rate into the pump. The IV line is then installed in the portable pump and the assembly placed in a pack or other carrying apparatus that may be retained on the patient. The medicament may be delivered as the patient proceeds through normal life activities until the full dose is complete. The patient may then return the assembly to the nurse or health care professional who may provide a new bag of medicament and IV line, and may reprogram the pump for new treatment.

Pumps suitable for ambulatory use can have high total operating costs driven in part by the cost of medical care required to have nurses or health care professionals review the medicament, program the pump with the prescribed dose and rate, and load the IV line cartridge onto the portable pump for every drug delivery. This process is repeated for every new bag of medicament that needs to be loaded increasing the cost of travel, either by the patient or the health care professional, between the hospital or clinic and the home of the patient.

Also, the need for high precision can require heavy and extensive plastic IV line cartridges or pumps that work against the costs of delivering medicine with patient loaded IV pumps. Heavy and extensive plastic materials can also make it difficult to install and remove the replaceable IV line cartridges which need high forces to compress the IV line and release anti-free flow locks to install the IV line properly.

SUMMARY OF THE INVENTION

The present inventors have determined that the ability for the patient to install their own medicament bag and IV line to the portable pump can greatly reduce healthcare professional time and patient travel costs. For example, home installation may be desired in situations when the patient cannot easily travel to the hospital or clinic and/or when access to health care professionals for at-home visits is limited, such as patients living in remote locations. In these situations, it is useful for the new bags of medicament and IV line to be shipped or delivered to the patient's home where the patients may self-install the new bag of medicament and IV line without the assistance of a health care professional.

The present invention provides an ambulatory pump intended to increase availability and acceptability of ambulatory infusion for patient loaded IV pumps. The pump has separable housing components, a reusable pump housing with the significant mechanical component of the pump and a disposable IV line cartridge with the IV-line, that can be constructed with less material reducing operating costs. Good dimensional stability can still be achieved by mounting the connectors of the IV line cartridge and pump housing, respectively, at opposed long edges of the housing facilitating precise alignment of the IV line and pumping elements.

The IV line cartridge is attachable to the pump housing using a hook locking system ensuring the patient can easily snap the IV line cartridge onto the pump housing and then quickly unlock the IV line cartridge without accidental release by using a rotating latch extending along a sidewall of the pump housing and flush with a front of the pump. This rotating latch also provide greater mechanical leverage that unlocks the locking system with less finger force.

Specifically, the present invention provides an IV line assembly having a pump housing releasably receiving an IV line clamp carrying an IV line adapted to communicate between an external IV bag and a patient connection. A substantially rigid housing has front and rear opposed walls extending along a longitudinal axis of the housing and separated by first and second opposed end walls and supports: a pump communicating with the IV line clamp to pump fluid through the IV line by peristaltic compression of the IV line when the IV line clamp is attached to the housing; a first set of attachment elements extending along the longitudinal axis of the housing and receiving a second set of attachment elements extending along a longitudinal side of the IV line clamp; and an actuator wherein the first attachment elements move generally along the longitudinal axis of the housing and the longitudinal side of the IV line clamp when the actuator is rotated about an axis of rotation extending along the longitudinal axis of the housing.

It is thus a feature of at least one object of the invention to provide a lever that can provide mechanical advantage to reduce the amount of finger force needed to overcome the locking force on the hooks while resisting accidental activation because of its rotary rather than linear action.

The first attachment elements may be biased into engagement with the second attachment elements independent from engagement of the actuator with the first attachment elements to disengage the first attachment elements from the second attachment elements.

It is thus a feature of at least one object of the invention to permit snapping the IV line clamp onto the pump housing without moving the lever. The hooks move independently of the lever so that the IV line clamp can be attached to the pump housing using one hand (for example, pressing the pump down against a table to engage the IV line clamp) without rotating the lever.

The actuator may be a lever having a proximal end pivotable about the axis of rotation and extending to a distal end extending perpendicular to the axis of rotation. The lever may extend along one of the first and second opposed end walls. The lever may be substantially flush with the front wall of the pump housing.

It is thus a feature of at least one object of the invention to prevent accidental disengagement of the IV line clamp from the pump housing where the sidewalls are protected from being hit when held within the carrying pouch (compared to the larger exposure area of the front and rear walls).

The lever may have a gripping flange extending away from the one of the first and second opposed end walls.

It is thus a feature of at least one object of the invention to prevent activation of the lever when within a carrying pouch during ambulatory use be requiring the user to consciously coax the lever out along the side of the pump by frictional sliding of the lever or catching the lever edge with a fingernail, practical because of the low activation force of the lever.

The proximal end of the lever may be coupled to a shaft rotating about the axis of rotation and may be spring biased in a direction away from a spring force biasing the first attachment elements into engagement with the second attachment elements tending to hold the IV clamp against the pump housing.

It is thus a feature of at least one object of the invention to allow the hooks to be separable from the lever during engagement of the IV clamp with the pump housing (the lever is not connected to the hooks).

The free distal end of the lever may provide a width at least 0.3 inches wide and extend at least 1.5 inches long from the axis of rotation.

It is thus a feature of at least one object of the invention to provide greater mechanical advantage by increasing the distance of the lever arm (distance between the axis of rotation and the force on the lever) reducing the amount of force needed to overcome the strong spring biasing force on the hooks. The finger length and width of the lever provides a larger gripping and finger engagement area.

The spring force biasing the first attachment elements into engagement with the second attachment elements may be greater than a second spring force on the lever biasing the shaft away from the first attachment elements. A force required to rotate the lever against the second spring force may be less than a force on the first attachment elements needed to disengage the second attachment elements.

It is thus a feature of at least one object of the invention to provide a robust attachment of the cartridge with the hooks by using a strong, stiff spring while allowing easy activation of the lever.

Movement of the first attachment elements to disengage the second attachment elements may be permitted only when the actuator is rotated at least 90 degrees about the axis of rotation. Movement of the first attachment elements to disengage the second attachment elements may be permitted only when the actuator is rotated at least 50% of its full range of rotation.

It is thus a feature of at least one object of the invention to reduce the likelihood of accidental disengagement of the IV line clamp from the housing by requiring extensive rotational motion of a lever that is unlikely to occur through collision alone.

One of the front and rear bottom edges of the housing may support the first set of attachment elements. Each of front and rear bottom edges of the housing may support attachment elements engaging corresponding attachment elements of the IV line clamp.

It is thus a feature of at least one object of the invention to assist with alignment of the locking elements by arranging the hinge elements spaced apart along the long edges of the housing to prevent twisting of the IV line cartridge with looseness (high tolerance) in the hinge points.

One of the front and rear opposed bottom edges may include a hinge portion releasably attaching to a second hinge portion on the IV clamp to allow engagement of the hinge portions before engagement of the peristaltic pump elements with the IV line. The hinge portion may include a bar for receiving the second hinge portion including a first and second hinge spaced longitudinally along one longitudinal wall of the IV line clamp.

It is thus a feature of at least one object of the invention to assist with alignment of the locking elements (hooks with receiving tabs) by the initial attachment of longitudinal hinge elements of the IV line clamp and pump housing, respectively, to make it easier to pivot the housing downward toward the IV line clamp (or the IV line clamp upward toward the bottom of the housing) for locking.

The first set of attachment elements of the housing may be hooks and the second set of attachment elements of the IV line clamp may be receiving tabs. The set of hooks and receiving tabs may include three hooks and three corresponding receiving tabs.

It is thus a feature of at least one object of the invention to provide a strong attachment force of the IV line clamp to the pump housing minimizing accidental detachment, especially during drug delivery and when the patient is active, thus squeezing the medical tubing against the peristaltic pumping elements and unlocking the anti-free flow lock.

Hooks of the set of hooks may be spring biased into engagement with the receiving tabs tending to hold the IV clamp against the pump housing. The hooks may be beveled to move the hooks against the spring biasing with attachment but not with detachment.

It is thus a feature of at least one object of the invention to allow attachment of the IV line clamp to the pump housing with a single hand, for example, by pressing the two parts together without an additional switch.

The pump housing may further include peristaltic actuator elements extending downwardly from the housing and communicating with the IV line of the IV line clamp to permit peristaltic pumping of liquid to the IV line; a user interface for receiving programming commands from a clinician; and an electronic computer communicating with the pump and the user interface and executing a program stored in a non-transitory computer readable storage medium to control operation of the pump.

These particular objects and advantages may apply to only some embodiments falling within the claims and thus do not define the scope of the invention.

BRIEF DESCRIPTION OF THE FIGURES

FIG. 3 is a perspective fragmentary view of the upper electronics portion and lower clamp portion as released showing various elements thereof;

FIG. 4 is a fragmentary cross-sectional view taken along 3-3 of FIG. 1 showing operation of the hook locking elements with the receiving tabs of FIG. 3; and FIG. 5 is an enlarged, fragmentary rear view of the cam mechanism of FIG. 4 showing rotary movement of a pin to strike a longitudinally translating button to release the hooks from engagement.

DETAILED DESCRIPTION OF THE PREFERRED EMBODIMENT

Figure 1:
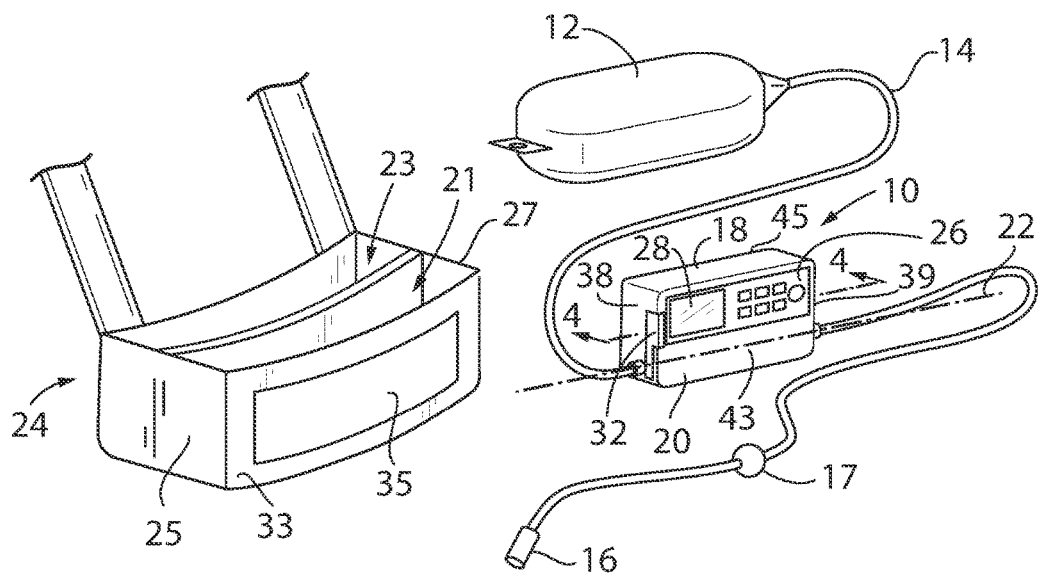
FIG. 1 is a simplified perspective view of the ambulatory pump assembly as provided to a patient.

Referring now to FIG. 1, an ambulatory pump 10 may operate in conjunction with a medicament bag 12 communicating with an IV line 14. The medicament bag 12 may be, for example, a flexible plastic bag of the type used to hold IV solutions, and the IV line 14 provides a flexible tube allowing the flow of medicament from the medicament bag 12 and a patient connector 16 that may communicate with the patient through a needle or port or the like. The IV line 14 may include a bubble filter 17 for removing included air bubbles, limiting the need for air bubble sensing.

The ambulatory pump 10 provides a two-part housing having an upper electronics portion 18 that may attach to a lower clamp portion 20 to receive the IV line 14 therebetween along a longitudinal axis 22 being generally the longest dimension of the housing of the ambulatory pump 10. As so received, the ambulatory pump 10 may pump liquid through the IV line 14 by peristaltic action.

In one embodiment, the ambulatory pump 10 is constructed to weigh less than a half pound and preferably less than 1.5 inches by 2 inches by 5 inches so as to be easily carried by the patient, for example, in a front compartment 21 of a pouch 24 also sized to receive the medicament bag 12, for example, in a rear compartment 23 of the pouch 24.

The ambulatory pump 10 may be held within the pouch 24 with sidewalls 25 and 27 of the pouch 24 closely cradling the corresponding longitudinally-opposed sidewalls of the ambulatory pump 10 and a front wall 33 of the pouch 24 having a clear screen 35 providing a window that allows the user to view a liquid crystal type display 28 of the ambulatory pump 10 and to, optionally, press membrane switch pushbuttons 30 of a user interface 26 of the ambulatory pump 10 through the clear screen 35.

Figure 2:
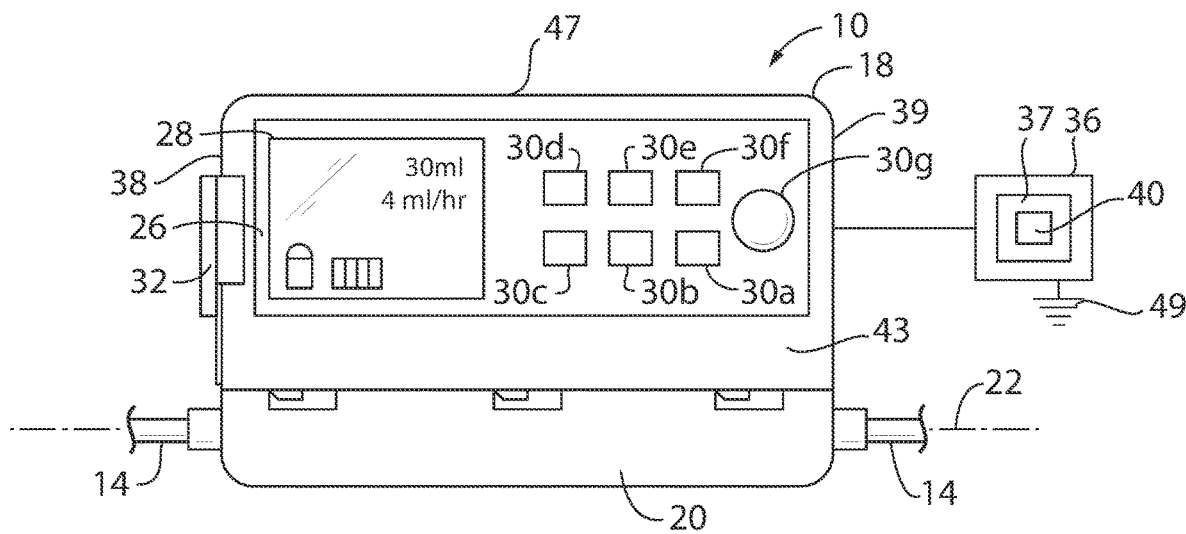
FIG. 2 is a front elevational view of the ambulatory pump showing inter-assembly of an upper electronics portion and lower clamp portion of the housing as separated by operation of release elements and showing a user interface comprising a display and manually operated buttons.

Referring now to FIGS. 2 and 3, the housing of the upper electronics portion 18 may present on its front wall 33 the user interface 26 comprising, for example, the liquid crystal type display 28 for displaying symbols and alphanumeric characters under computer control. The user interface 26 also provides multiple membrane switch pushbuttons 30 that may be activated by a user. Generally, the pushbuttons include a limited number of controls including, in one embodiment, run and stop pushbuttons 30a and 30b, respectively, that will stop and start operation of the pump as will be described below; a rate pushbutton 30c allows setting of the maximum pumping rate of the ambulatory pump 10 in milliliters per hour by cycling through menu standard rates with each push. The pushbuttons also include a "volume to be infused" pushbutton 30d allowing user control of the maximum volume to be infused during a treatment protocol, also by cycling through standard settings with each push, as well as an information pushbutton 30 allowing the display of detailed information about the pump including remaining pump life. Pushbutton 30f allows the unit to be turned on and off to conserve power. A bolus pushbutton 30g allows short operation of the pump to deliver medicament in fixed patient-controlled bolus quantities.

The ambulatory pump 10 may include a microcontroller 36 being an electronic computer having a self-contained nonvolatile memory 37 holding an operating program 40 and necessary storage variables as will be described below. The nonvolatile memory may comprise, for example, flash memory and/or read only memory, or other similar nonvolatile memory as context requires, which may store data values to be retained even in the absence of electrical power.

The microcontroller 36 also provides various inputs and output lines communicating, for example, with the display 28 for providing display information thereon and various pushbuttons 30 for receiving data related to their activation by user. In addition, the microcontroller 36 may provide control lines to a pump assembly having, for example, an internal DC electric motor (not shown) operating through a gear system to activate peristaltic plunger elements 44 that may press against the contained IV line 14 to push fluid therethrough. As is understood in the art, generally the peristaltic plunger elements 44 extend in an undulating serpentine fashion to compress and release the tubing thereby moving fluid therethrough.

The microcontroller 36 may also communicate electrically with various sensors. For example, upstream and downstream pressure sensors 46 and 48 which can be used to ensure proper operation of the pump by detecting abnormal pressures. Generally, each of the pressure sensors 46 and 48 may provide a spring-loaded plunger that presses into the outer wall of the IV line 14 to sense pressure.

All electrical components in the upper electronics portion 18 may be supplied with power by a contained storage battery 49 that may provide its power directly or through standard power processing circuits such as regulators and the like.

An ambulatory pump 10 suitable for use with the present invention is described generally in U.S. patent application Ser. No. 14/471,102 and titled "Low-cost Ambulatory Medical Pump" filed Aug. 28, 2014, assigned to the assignee of the present invention, and hereby incorporated by reference.

A lower left side edge of the upper electronics portion 18 provides for a release lever 32 as will be described below to remove the lower clamp portion 20 from attachment.

Still referring to FIGS. 2 and 3, the bottom wall 101 of the upper electronics portion 18 may provide a substantially planar lower interface having upstanding longitudinally-opposed sidewalls 38 and 39, these sidewalls separating the opposed upstanding longitudinally-extending front and rear walls 43 and 45. The bottom wall 101, longitudinally-opposed sidewalls 38 and 39, longitudinally-extending front and rear walls 43 and 45, and a top wall 47 provide a rectangular housing supporting a number of pump elements described below.

The bottom wall 101 of the upper electronics portion may engage with an upper surface of the lower clamp portion 20 providing a shallow tray having upstanding peripheral longitudinally-opposed end walls 90 and 92, these walls separating the opposed upstanding peripheral longitudinally-extending sidewalls 94 and 96.

The bottom wall 101 of upper electronics portion 18 may hold peristaltic plunger elements 44 and the downwardly extending operators of pressure sensors 46 and 48 aligning with the IV line 14 of the lower clamp portion 20, the IV line 14 held by guides 100 of the lower clamp portion 20 which forms notches to align and retain the IV line 14 longitudinally within the tray. The end walls 90 of the lower clamp portion may include notches further receiving retention bushings 98a and 98b formed in the IV line 14 to prevent longitudinal movement of the IV line 14 with respect to the lower clamp portion 20 along the longitudinal axis 22. The IV line 14 may also pass through a spring bias clamp element 102 that automatically clamps the IV line 14 when the lower clamp portion 20 is separated from the upper electronics portion 18.

The rear edge of the bottom wall 101 of the upper electronics portion 18 may support a hinge pin 106 spaced below the bottom wall 101 and extending generally parallel to the longitudinal axis 22 to receive downwardly extending open hinge collars 104 of the lower clamp portion 20 spaced along the rear sidewall 96 and extending away from the longitudinally-extending sidewalls 94 and 96 toward an exterior of the tray. The open hinge collars 104 may attach to and hinge about the hinge pin 106.

The front edge of the bottom wall 101 of the upper electronics portion 18 may support downwardly extending hooks 108 activated by release lever 32 as will be described below. When the lower clamp portion 20 is attached by the interconnection of open hinge collars 104 and hinge pin 106, and the bottom wall 101 of the upper electronics portion 18 is pivoted downward toward the lower clamp portion 20, the hooks 108 may pass over and attach to corresponding longitudinally-extending tabs 107 of the front sidewall 94 of the lower clamp portion 20 to retain the upper electronics portion 18 and lower clamp portion 20 together with the IV line 14 in proper alignment therebetween.

The hooks 108 may provide generally J-shaped or reversed L-shaped metal hooks engaging correspondingly shaped J-shaped of reversed L-shaped openings of the tabs 107 with the tabs 107 holding a point 109 of the hooks 108 from separation of the hooks 108 from the tabs 107.

Referring also to FIG. 4, the downwardly extending hooks 108 at the front edge of the bottom wall may be attached to a common driver bar 110 that is longitudinally extending and spring biased by a compression spring 112 into engagement with the tabs 107 tending to hold the lower clamp portion 20 against the upper electronics portion 18. The spring 112 may communicate with the bar 110 to bias the bar 110 leftward to hold the hooks 108 within the tabs 107. In one embodiment, a spring constant of the compression spring 112 may be approximately 0.3 to 0.4 N/mm and approximately 0.375 N/mm (9.5 N/inch). A force required to compress the spring 112 may be approximately 1.5 N to 2.5 N.

The lower clamp portion 20 may be attached to the upper electronics portion 18 by pressing the hooks 108 into the tabs 107 such that the hooks 108 move rightward against the force of the spring 112 into engagement with the tabs 107. The hooks 108 may be beveled at a downward slope from the point 109 to the shank 111 to help move the hooks into the tabs 107 against the spring biasing attachment of the lower clamp portion 20 but not with detachment of the lower clamp portion 20.

The driver bar 110 may communicate with, but may not be connected to, a release lever 32 which may be rotated about an axis of rotation 50 to translated longitudinal force rightward against the driver bar 110 against the biasing spring 112 to allow release of the hooks 108 from the tabs 107.

Rightward motion of the bar 110 is possible when an upper free distal end 114 of the release lever 32 is rotated downward in a forward direction as shown by arrow 116 and thus rotating a proximal end 115 of the release lever 32 about the axis of rotation 50. The proximal end 115 of the release lever 32 is attached to a longitudinally extending shaft 118 that extends through an opening in the sidewall 38 of the upper electronics portion 18 and is aligned with the driver bar 110 so that rotation of the shaft 118 about axis of rotation 50 causes rotation of a cam mechanism 120.

Referring briefly to the rear view of the cam mechanism of FIG. 5, in one embodiment, the cam mechanism 120 may be made up of a radially extending extended pin 122 of the shaft 118 that slides along a helical groove 123 of a collar 125 that connects to a protruding button 126 to extend that button with downward motion of the lever 32 and rotation of the shaft 118. The button 126 then presses against but does not connect to the driver bar 110 so the driver bar 110 may move freely to the right (as seen in the front view of FIG. 4) during snap in engagement but is driven by the lever 32 during release. It is understood that other cam mechanisms 120 may be utilized to translate the rotary motion of the shaft 118 into linear motion of the button 126 causing the button 126 to protrude, such as an irregularly shaped shaft or wheel, striking the button 126, as the shaft or wheel is rotated.

Referring again to FIG. 4, a torsion spring 128 positioned between the cam mechanism 120 and the release lever 32 on the shaft 118 stores mechanical energy when the release lever 32 is pulled downward, rotating the shaft 118 in a first direction, to disengage the hooks 108 from the tabs 107. The torsion spring 128 exerts an opposite (biasing) torque on the release lever 32 to return the release lever 32 to an upward position, rotating the shaft 118 in a second opposite direction, and thus causing the button 126 to retract from pressing on the bar 110 and the hooks 108 to engage the tabs 107. In one embodiment, the spring constant (torsion coefficient) of the torsion spring 128 may be approximately 0.2 to 0.4 N/cm/degree or 0.3 N·cm/degree (108 N·cm/turn). An activation force (torsion force) to rotate the release lever 32 may be approximately 27 N·cm to 67.5 N·cm.

The release lever 32 generally extends perpendicular to the shaft 118 and generally conforms and extends along the sidewall 38 of the upper electronics portion 18. The release lever 32 may extend upward at least 1 inch and at least 2 inches and at least 3 inches so that the distal end 114 is displaced from the axis of rotation 50. The lever 32 provides an extended lever arm (distance between the axis of rotation and the force on the lever) therefore reducing the amount of force required to overcome the force of the compression spring 112 on the hooks 108. Therefore, a force required to rotate the release lever 32 is less than a longitudinal force required to move the button 126 against the bar 110 and may be a ratio of 1:2 or 1:3.

A front flange 130 of the release lever 32 extends from a front edge of the release lever 32 and extends rightward along the front of the front wall 43 of the upper electronics portion 18 and is substantially flush with the front of the front wall 43 of the upper electronics portion 18. The front flange 130 stops the release lever 32 from further rearward rotation caused by the biasing force of the torsion spring 128 by stopping the lever 32 at an upward position. The front flange 130 may have generally curved outer edges and extend approximately at least 0.3 inches and at least 0.5 inches and between 0.3 to 0.8 inches to ensure that the front flange 130 catches the front wall 43. The width of the front flange 130 also widens the finger contact area of the lever 32.

The release lever 32 further includes a rear flange 132 extending outwardly from a rear edge of the release lever 32 away from the sidewall 38 of the upper electronics portion 18 and providing an edge making it easier for the user to grip and rotate the release lever 32 along arrow 116 with a finger or fingers. The rear flange 132 may extend less than 0.3 inches and less than 0.2 inches and between 0.1 to 0.3 inches to provide just enough of a grip edge to facilitate finger movement but to prevent inadvertent actuation. The width of the rear flange 132 also widens the finger contact area of the release lever 32.

A total width of the lever 32 may be at least 0.3 inches and at least 0.5 inches and at least 0.8 inches to provide a broad finger contact area of approximately at least 0.3 inches$^2$ and at least 0.5 inches$^2$ and approximately 0.5 inches$^2$ to 1.5 inches$^2$.

The release lever 32 may have a full range of motion of at least 180 degrees and at least 90 degrees, and the release lever 32 may be required to rotate at least 90 degrees and approximately 90 degrees in order to cause the button 126 to extend at least a distance 133 corresponding with a gape width 134 of the hooks 108 allowing for the release of the hooks 108 from the tabs 107. In this respect, the release lever 32 may require rotation of at least 50% and approximately 100% of its full range of motion in order to translate the button 126 at least a distance of the gape width 134 and to release the hooks 108 from the tabs 107.

Because the motion of the release lever 32 is rotational, and the release lever 32 is located at a position along the sidewall of the upper electronics portion 18, accidental release of the lower clamp portion 20 is greatly reduced, especially when placed within the pouch 24 shielding the sidewall 38 from accidental collisions or pressing forces. The rotational motion, of example at least 90 degrees, of the release lever 32 required to release the hooks 108 from the receiving tabs 107 is also unlikely to occur accidentally.

This is in contrast with push or sliding buttons which may be pressed or collided with accidentally, and with release buttons that are positioned on the top or front of the pump housing which are more greatly exposed to forces.

Certain terminology is used herein for purposes of reference only, and thus is not intended to be limiting. For example, terms such as "upper", "lower", "above", and "below" refer to directions in the drawings to which reference is made. Terms such as "front", "back", "rear", "bottom" and "side", describe the orientation of portions of the component within a consistent but arbitrary frame of reference which is made clear by reference to the text and the associated drawings describing the component under discussion. Such terminology may include the words specifically mentioned above, derivatives thereof, and words of similar import. Similarly, the terms "first", "second" and other such numerical terms referring to structures do not imply a sequence or order unless clearly indicated by the context. Indication is used herein to mean any type of sense to indication including an audio alarm, visual display or other computer-controlled activation (motor buzz, etc.)

When introducing elements or features of the present disclosure and the exemplary embodiments, the articles "a", "an", "the" and "said" are intended to mean that there are one or more of such elements or features. The terms "comprising", "including" and "having" are intended to be inclusive and mean that there may be additional elements or features other than those specifically noted. It is further to be understood that the method steps, processes, and operations described herein are not to be construed as necessarily requiring their performance in the particular order discussed or illustrated, unless specifically identified as an order of performance. It is also to be understood that additional or alternative steps may be employed.

References to "a microprocessor" and "a processor" or "the microprocessor" and "the processor," can be understood to include one or more microprocessors or other types of computers, gate arrays or the like that can execute programs and communicate with each other. Furthermore, references to memory, unless otherwise specified, can include one or more processor-readable and accessible memory elements and/or components that can be internal to the processor-controlled device, external to the processor-controlled device, and can be accessed via a wired or wireless network. The term manual pushbuttons means buttons that may be operated by finger touch or the like including touchscreen and passive switch and mechanical switch.

It will be appreciated that the look-ahead operation of the ambulatory pump 10 described herein is consistent both with anticipatory locking of the pump so that the pump does not exceed the service values, as well as setting the service values to a value below the actual longest desired service value by amount of the typical treatment protocol and allowing the treatment protocol to exceed the service value once, and then locking out pump. In this latter case, the pump lockout anticipates that the next treatment protocol would exceed the remaining operating time or volume (which is a negative value) and need not actually accept a new protocol.

It is specifically intended that the present invention not be limited to the embodiments and illustrations contained herein and the claims should be understood to include modified forms of those embodiments including portions of the embodiments and combinations of elements of different embodiments as come within the scope of the following claims. All of the publications described herein, including patents and non-patent publications, are hereby incorporated herein by reference in their entireties.

We claim:

1. An IV line assembly having a pump releasably receiving an IV line adapted to communicate between an external IV bag and a patient connection, comprising:
   an IV line clamp housing supporting an IV line clamp and having front and rear opposed walls extending parallel to a longitudinal axis of the IV line clamp housing and separated by first and second opposed end walls extending perpendicular to the longitudinal axis of the IV line clamp housing and releasably receiving:
   a pump housing supporting the pump, the pump communicating with the IV line to pump fluid through the IV line by peristaltic compression of the IV line when the IV line clamp housing is coupled to the pump housing;
   a first set of attachment elements supported by the pump housing and received by a second set of attachment elements supported by at least one of the front and rear opposed walls of the IV line clamp housing; and
   an actuator wherein the first attachment elements are spring biased to engage the second set of attachment elements by a biasing spring and configured to move parallel to the longitudinal axis of the IV line clamp housing when the actuator is rotated about an axis of rotation extending parallel to the longitudinal axis of the IV line clamp housing to disengage the second set of attachment elements;
   wherein the actuator comprises a lever biased by a torsion spring having a proximal end pivotable about the axis of rotation and extending to a free distal end spaced from the axis of rotation; and
   wherein the first attachment elements may be biased into engagement with the second attachment elements independent of rotation of the lever.

2. The IV line assembly of claim 1 wherein the lever extends along one of the first and second opposed end walls.

3. The IV line assembly of claim 2 wherein the lever has a gripping flange extending away from the one of the first and second opposed end walls.

4. The IV line assembly of claim 2 wherein the lever is substantially flush with the front wall of the pump housing.

5. The IV line assembly of claim 2 wherein the free distal end of the lever extends at least 1 inch from the axis of rotation.

6. The IV line assembly of claim 1 wherein the proximal end of the lever is coupled to a shaft rotating about the axis of rotation and spring biased away from applying a moving force on the first attachment elements along the longitudinal axis.

7. The IV line assembly of claim 6 wherein a spring force biasing the first attachment elements into engagement with the second attachment elements is greater than a second spring force on the lever biasing the shaft away from applying a moving force on the first attachment elements.

8. The IV line assembly of claim 6 wherein an activation force required to rotate the lever is less than the moving force on the first attachment element needed to disengage the first attachment elements from the second attachment elements.

9. The IV line assembly of claim 6 wherein disengagement of the first attachment elements and the second attachment elements is permitted only when the actuator is rotated at least 90 degrees about the axis of rotation.

10. The IV line assembly of claim 6 wherein disengagement of the first attachment elements and the second attachment elements is permitted only when the actuator is rotated at least 50% of its full range of rotation.

11. The IV line assembly of claim 1 wherein the first set of attachment elements are supported on a bottom wall of the pump housing.

12. The IV line assembly of claim 11 wherein a bottom edge of the pump housing includes a hinge portion releasably attachable to a second hinge portion on a top edge of the IV line clamp housing to allow engagement of the hinge portions before engagement of the pump with the IV line.

13. The IV line assembly of claim 12 wherein the hinge portion includes a bar for receiving the second hinge portion including a first and second hinge spaced longitudinally along one longitudinal wall of the IV line clamp.

14. The IV line assembly of claim 1 wherein the first set of attachment elements of the housing are hooks and the second set of attachment elements of the IV line clamp are receiving tabs.

15. The IV line assembly of claim 14 wherein the set of hooks and receiving tabs includes three hooks and three corresponding receiving tabs.

16. The IV line assembly of claim 14 wherein the hooks are beveled to move the hooks against the bias of the biasing spring upon attachment of the pump housing to the IV clamp housing and the bevel of the hooks does not move the hooks against the bias of the biasing spring upon detachment of the pump housing from the IV line clamp housing.

17. The IV line assembly of claim 1 wherein the pump housing further comprises:
peristaltic actuator elements extending downwardly from the housing and communicating with the IV line of the IV line clamp to permit peristaltic pumping of liquid to the IV line;
a user interface for receiving programming commands from a clinician; and
an electronic computer communicating with the pump and the user interface and executing a program stored in a non-transitory computer readable storage medium to control operation of the pump.

* * * * *